United States Patent [19]

Svendsen

[11] Patent Number: 5,633,708
[45] Date of Patent: May 27, 1997

[54] APPARATUS FOR MEASURING REFRACTIVE INDEX

[76] Inventor: David A. Svendsen, "Ashdene" St. Giles Hill, Winchester, Hampshire S023 0HH, United Kingdom

[21] Appl. No.: 637,815

[22] PCT Filed: Nov. 3, 1994

[86] PCT No.: PCT/GB94/02412

§ 371 Date: May 3, 1996

§ 102(e) Date: May 3, 1996

[87] PCT Pub. No.: WO95/13529

PCT Pub. Date: May 18, 1995

[30] Foreign Application Priority Data

Nov. 8, 1993 [GB] United Kingdom ............ 9322936

[51] Int. Cl.[6] ........................................... G01N 21/43
[52] U.S. Cl. ............................. 356/73.1; 356/128
[58] Field of Search ........................ 356/73.1, 128

[56] References Cited

U.S. PATENT DOCUMENTS 3,879,128 4/1975 Presby et al. ............. 356/73.1
4,553,841 11/1985 Coppa et al. ............. 356/73.1 X

FOREIGN PATENT DOCUMENTS

WO90/05904 5/1990 WIPO .

Primary Examiner—Vincent P. McGraw
Attorney, Agent, or Firm—Iandiorio & Teska

[57] ABSTRACT

Apparatus for the measurement of optical properties of a quasi cylindrically symmetric transparent object (2), which apparatus comprises source means (11) for providing a source of electromagnetic radiation, illumination forming means for forming an illuminating beam (41), region selecting means for selecting a localised radial region (42), region scanning means for scanning the localised radial region (42) through a range of radial positions, reflection detecting means for detecting a reflected beam (43), beam measuring means for measuring the component of the position where the reflected beam (43) leaves the transparent object (2), supporting means which causes the illuminating beam (41), the reflected beam (43) and an axis of rotational symmetry (1) of the transparent object (2) to lie in a measurement plane, and angle altering means for altering the angle of incidence of the illuminating beam (41) on the transparent object (2).

12 Claims, 5 Drawing Sheets

APPARATUS FOR MEASURING REFRACTIVE INDEX

This invention relates to apparatus for the measurement of optical properties, for example the radial refractive index profile, of a quasi cylindrically symmetric transparent object, such for example as an optical fibre preform. In particular, the invention enables the measurement of certain types of optical fibre preforms which are not amenable to analysis by the apparatus and methods of prior art.

An apparatus which analyses the optical properties of a quasi cylindrically symmetric transparent object by the illumination of the object generally within the plane orthogonal to the axis of rotational symmetry of the object is termed a transverse-type analyser. Specific examples of transverse-type analysers used for the measurement of the refractive index of an optical fibre preform are disclosed in patent specification GB-A-2071315, and by P. L. Chu in Electronics Letters, 24th November 1977, Vol.13, No.24, pp.736 to 738, and are the ones that have been used most widely in the past ten years. Improvements to the apparatus and methods have been disclosed recently in patent specifications PCT/GB89/01352 and PCT/GB91/00716.

There are two major limitations to the current transverse-type analysers when used for measuring the refractive index of an optical fibre preform. Firstly, there are a number of different types of optical fibre preforms which are of considerable importance but which cannot be satisfactorily measured by prior art. In some cases the measurement is possible but is in error, and in other cases the apparatus fails to detect an appropriate beam of electromagnetic radiation and so the measurement itself fails. The reason for this is that a significant part of the measurement beam interacts with regions of varying refractive index at almost a right angle to a radius of the optical fibre preform within the plane orthogonal to an axis of rotational symmetry of the optical fibre preform. With certain optical fibre preform types, this results in undesirable reflection and diffraction, which then lead to measurement problems. Secondly, in almost all cases it is necessary to surround the optical fibre preform being measured by a region of refractive index liquid in order to obtain a satisfactory optical interface between the optical fibre preform and the measurement apparatus. This is because the measurement beam passes through substantially every part of the circumference at some point during the course of a measurement.

The present invention seeks to overcome both types of limitation by using a significantly different type of interaction between the measurement beam and the transparent object to that used by current transverse-type analysers. An aim of the present invention is to provide apparatus suitable for the measurement of quasi cylindrically symmetric transparent objects not measurable by currently available apparatus. Another aim of the present invention is to provide improvements to the optical interface between the quasi cylindrically symmetric transparent object and the measurement apparatus.

According to a non-limiting embodiment of the present invention, there is provided apparatus for the measurement of optical properties of a quasi cylindrically symmetric transparent object, comprising source means for providing a source of electromagnetic radiation, illumination forming means for forming an illuminating beam of electromagnetic radiation for illuminating the transparent object, region selecting means for selecting a localised radial region within the transparent object illuminated by the illuminating beam, region scanning means for scanning the localised radial region through a range of radial positions within the transparent object, reflection detecting means for detecting a reflected beam of electromagnetic radiation reflected out of the illuminating beam at the localised radial region, beam measuring means for measuring the component of the position of the point where the reflected beam leaves the transparent object along a direction parallel to an axis of rotational symmetry of the transparent object, supporting means which causes the illuminating beam, the reflected beam and an axis of rotational symmetry of the transparent object, to lie in a measurement plane whose thickness is generally small compared with the radius of the transparent object, angle altering means for altering the angle of incidence of the illuminating beam on the transparent object within the measurement plane, control means for controlling the components of the apparatus such that the measurements are made at the required time and in the required sequence, and computing means for computing optical properties of the transparent object.

The transparent object may take the form of a glass rod, a grin rod lens, an optical fibre preform in a glass state, an optical fibre preform in a soot state, or an optical fibre.

The electromagnetic radiation may be any electromagnetic radiation of a range of wavelengths to which the transparent object is transparent. Preferably, the electromagnetic radiation has the wavelength of 633 nm, being the wavelength of a Helium Neon laser, or 1300 nm or 1550 nm, being wavelengths of specific interest for optical fibre technology, or the wavelength of X-rays, which are useful for measuring an optical fibre preform in a soot state before it has been consolidated to a glass state.

The source means may be of low coherence, such as a tungsten halogen bulb white light source, or be of high coherence, such as a gas laser or a semiconductor diode laser, and may provide electromagnetic radiation either continuously or in pulses. In addition, the source means may be such that the wavelength of the electromagnetic radiation may be varied, such as that provided by a light emitting diode and a monochromator.

The control means may comprise personal computers, microprocessors, analogue to digital convertors, digital to analogue convertors, electric motors, and/or other electronic and electromechanical components. The computing means may comprise personal computers, microprocessors, dedicated electronic processors, and/or other computing devices, as are well known to someone skilled in the art of measurement instrumentation.

The supporting means may include adjusting means for adjusting the thickness of the measurement plane to be of the least thickness that is permitted by the dimensions of the illuminating beam, the reflected beam, and the transparent object, and by the degree of cylindrical symmetry of the transparent object. In addition, the supporting means may include object translating means for translating the transparent object in the measurement plane relative to the apparatus of the present invention along an axis of rotational symmetry of the transparent object. The supporting means may also include object rotating means for rotating the transparent object in the measurement plane relative to the apparatus of the present invention around an axis of rotational symmetry of the transparent object.

The region scanning means may include object moving means for moving the transparent object relative to other components of the apparatus along a direction orthogonal to an axis of rotational symmetry of the transparent object and within the measurement plane such that the localised radial region in the transparent object may be located over a range of radial positions.

In an embodiment of the present invention, the apparatus is one in which the illumination forming means includes illumination collimating means for collimating the illuminating beam for illumination of the transparent object, and in which the region selecting means, region scanning means, reflection detecting means and the beam measuring means are included as detector array means for measuring the component of the position of the point at which the reflected beam falls on the detector array means along a direction parallel to an axis of rotational symmetry of the transparent object. The detector array means may be any means that converts the spatial distribution of electromagnetic radiation incident upon it into an electrical signal, such as a semiconductor photodiode array, a charge-coupled device array, or an array of photomultiplier tubes.

In another embodiment of the present invention, the apparatus is one in which the illumination forming means includes illumination focusing means for focusing the illuminating beam to form the localised radial region within the transparent object, in which the reflection detecting means includes photodetector means for converting electromagnetic radiation into an electrical signal, in which the region selecting means includes reflection focusing means for focusing the reflected beam on to a sensitive surface of the photodetector means, in which the region scanning means includes the object moving means, and in which the beam measuring means includes interrupting means for interrupting the reflected beam such that different parts of the reflected beam, with respect to a direction parallel to an axis of rotational symmetry of the transparent object, may be prevented from reaching the photodetector means. The interrupting means may be a knife edge aperture moved so as to alter the intensity of the reflected beam detected by the photodetector means. Alternatively, the interrupting means may create a periodic signal such as that detected by the photodetector means when a chopper wheel alternately blocks and exposes the reflected beam. The photodetector means may be a semiconductor photodiode, a photoresistive device, or a photomultiplier tube. The region selecting means may also include beam blocking means for preventing reflected beams reaching the photodector means without affecting the reflected beam from the localised radial region being measured.

The apparatus of the present invention may include optical interface means for producing a well-defined optical interface between the illuminating and reflected beams and the surface of the transparent object such that the optical effects of imperfections at the surface of the transparent object are reduced. The optical interface means may be similar to those used in current transverse-type analysers where the whole of the circumference of the transparent object is surrounded by a refractive index liquid. Preferably, the optical interface may comprise a solid interface means and a volume of refractive index material so as to form an optical interface to only that small portion of the circumference of the transparent object that is passed through by the illuminating and reflected beams. More preferably, the solid interface means may be positioned sufficiently close to the surface of the transparent object so that a thin film of refractive index material, and/or the solid interface means, may be held in place by surface tension and/or gravity alone. The solid interface means may take any appropriate shape and size, and be made of any appropriate transparent material, such as a plane sheet of glass or a glass lens. The refractive index material may be any transparent liquid or gel or grease or malleable material or adhesive such that its refractive index approximates to that of the transparent object being measured.

Embodiments of the invention will now be described solely by way of example and with reference to the accompanying drawings in which.

Figure 1:
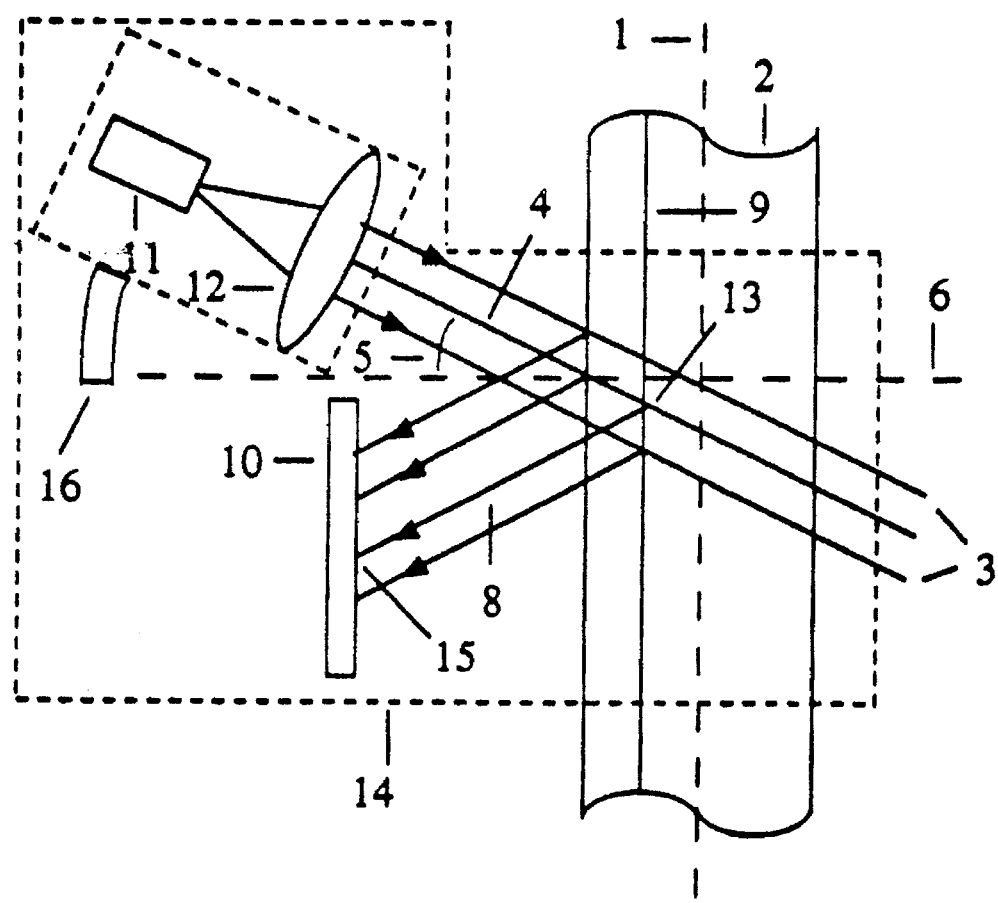
FIG. 1 is a diagram of the projection of an embodiment of the present invention in the measurement plane, in which the region selecting means, region scanning means, reflection detecting means and the beam measuring means are included as detector array means.
Figure 2:
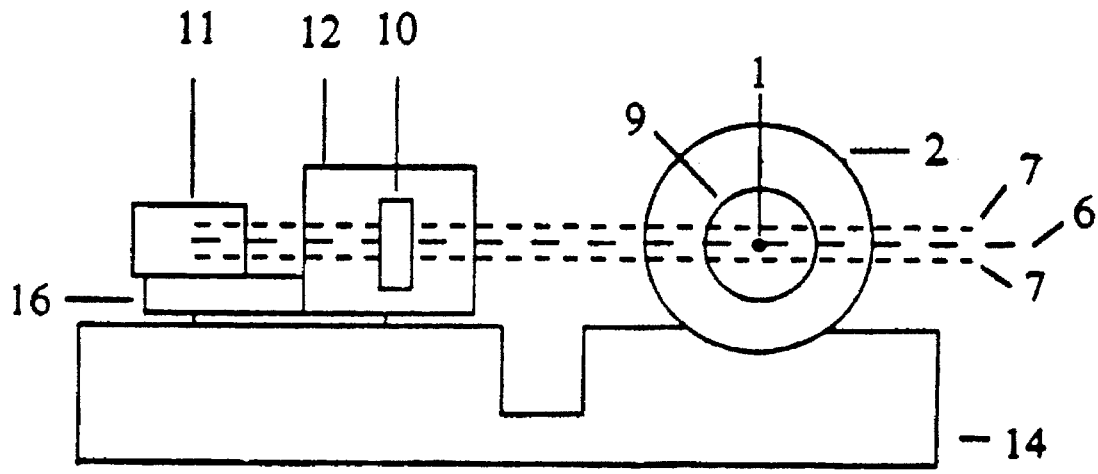
FIG. 2 is a diagram of the projection of the same embodiment as that of FIG. 1 in the plane orthogonal to an axis of rotational symmetry of the transparent object.

With reference to FIGS. 1 and 2, a source means, in the form of a laser 11, and an illumination collimating means, in the form of a lens 12, provide a collimated beam of electromagnetic radiation 3, a part of which is an illuminating beam 4, which illuminates the transparent object 2, at an incident angle 5 to an axis 6, which is orthogonal to an axis of rotational symmetry 1 of the transparent object 2 and which lies in a measurement plane 7. The incident angle 5 is varied by the angle altering means 16 in the form of a movement of the laser 11 and the lens 12 such that the collimated beam 3 pivots about any convenient point in the measurement plane 7. A reflected beam 8 of electromagnetic radiation, reflected out of the illuminating beam 4 by a change of refractive index 9 in the transparent object 2 at a localised radial region 13, falls on region selecting means, region scanning means, reflection detecting means and beam measuring means, in the form of a detector array means 10, at a position 15 which depends upon the known positions of the components of the apparatus, upon the incident angle 5, and upon the path traversed by the illuminating beam 4 and the reflected beam 8. A supporting means 14 holds the laser 11, the lens 12, the angle altering means 16, the detector array means 10, and the transparent object 2 such that the illuminating beam 4, the reflected beam 8, and the axis of rotational symmetry 1, lie in the measurement plane 7. The distribution of intensity detected by the detector array means 10 as a function of the position 15 on the detector array means 10 is recorded for two or more different values of incident angle 5 by computing means (not shown) and controlling means (not shown), and the radial position of the change of refractive index 9 and the refractive index of the layer traversed by illuminating beam 4 and reflected beam 8 are computed by computing means (not shown) as described below with reference to FIG. 3.

Figure 3:
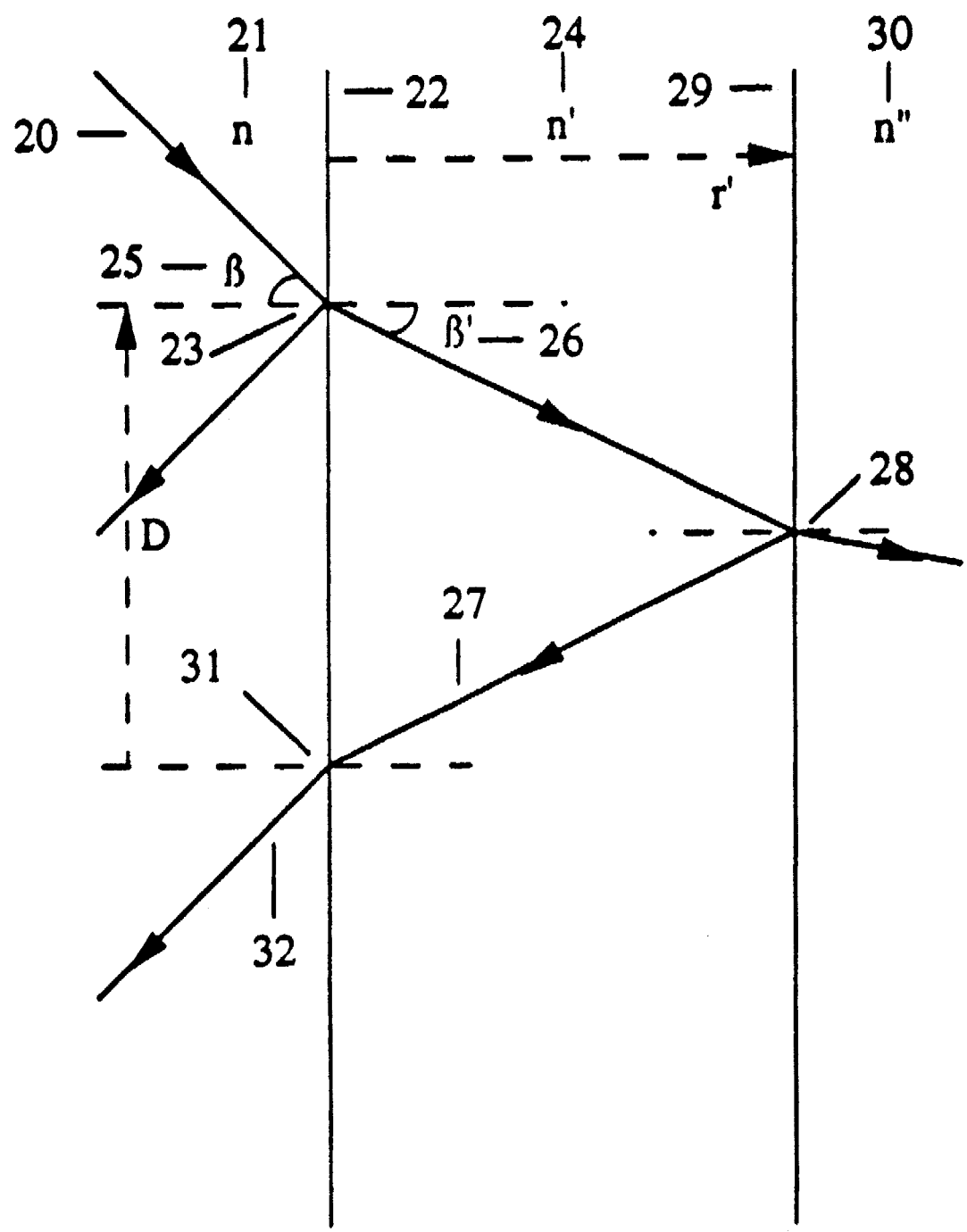
FIG. 3 is a diagram of the refraction and reflection at a single layer of refractive index change inside the transparent object.

FIG. 3 shows a beam 20 of electromagnetic radiation traversing a layer 21 of uniform refractive index n, striking an interface 22 with a second layer 24 of refractive index n' at a point 23, and at an angle of incidence β 25. The beam 20 is refracted at the interface 22 and traverses the layer 24 at an angle β' 26 until a beam 27 is reflected at a point 28 at a further interface 29 with a third layer 30 of refractive index n". The beam 27 returns to the interface 22 where it is refracted at a point 31, and becomes a reflected beam 32 leaving interface 22 at the angle of incidence β 25. The following expression for the distance between the point 23 and the point 31 D may be obtained from Snell's Law and simple geometry:

$$D = 2r' \text{SIN}(\beta)(n/n')/(\sqrt{(1-(n/n')^2 \text{SIN}^2(\beta))}) \quad \text{(i)}$$

where r' is the perpendicular distance between interfaces 22 and 29, and represents the thickness of the layer 24. Expression (i) may be rearranged to give:

$$(1/\text{SIN}^2(\beta)) = (n/n')^2(1 + 4r'^2/D^2) \quad \text{(ii)}$$

from which (n/n') and r' may be obtained from the values of D measured for two or more different values of incident angle β 25. With reference to use of the apparatus described in FIG. 1, the distribution of intensity with the position 15 on the detector array means 10 is recorded for a first value of the incident angle 5. The point 23 is identified for the localised radial region 13 being on the surface of the transparent object 2, such that layer 21 is air and hence of known refractive index, by the computing means (not shown). The second point 31 is similarly identified for the reflected beam 32, reflected at point 28 from the next interface 29. The two points 23 and 31 are then identified for a second value of incident angle 5 and the expression (ii) solved, using the known scaling which relates the position 15 on the detector array means 10 to position along the axis of rotational symmetry 1. Alternatively, further records may be taken for a number of values of incident angle 5 and sets of expression (ii) solved using well-known least-squares mathematical techniques. In a similar way, the thickness and refractive index of a second and subsequent layer may be computed in a recursive manner. It is obvious from the distribution recorded by the detector array means 10 which part of the distribution relates to which layer of the transparent object when the transparent object 2 contains a few layers of refractive index and the layers are well-spaced. However, it may become necessary to use a prior knowledge about the transparent object 2, such as the approximate number and thickness of the layers. In addition, where the thickness r' is small compared with the coherence length of the source means it will be necessary to take into account the constructive and destructive interference that takes place between the different parts of the reflections from the collimated beam 3 by choosing the range of values of incident angle 5 appropriately, as is well-known from the theory of reflection gratings. Alternatively and with advantage, this interference may be used to measure the distance D. With reference to FIG. 3, the optical path difference between the ray reflected at the point 23 and the ray reflected at the point 28 is given by:

$$\text{Optical path difference} = D \, n \, (((n'/n)^2/\text{SIN}(\beta)) - \text{SIN}(\beta)) \quad \text{(iii)}$$

The ray reflected at the point 23 and the ray reflected at the point 28 will interfere constructively when the optical path difference is an integral number of wavelengths, and will interfere destructively when the optical path difference is an integral number of wavelengths plus one half of a wavelength. Thus the change in optical path difference as the incident angle β 25 is changed may be measured to half a wavelength of the light source by counting the number of occurrences of constructive and destructive interference as the incident angle β 25 is changed. In this way, values of (n/n') and r' may be obtained from expression (ii) and expression (iii) for three or more different values of incident angle β 25.

Figure 4:
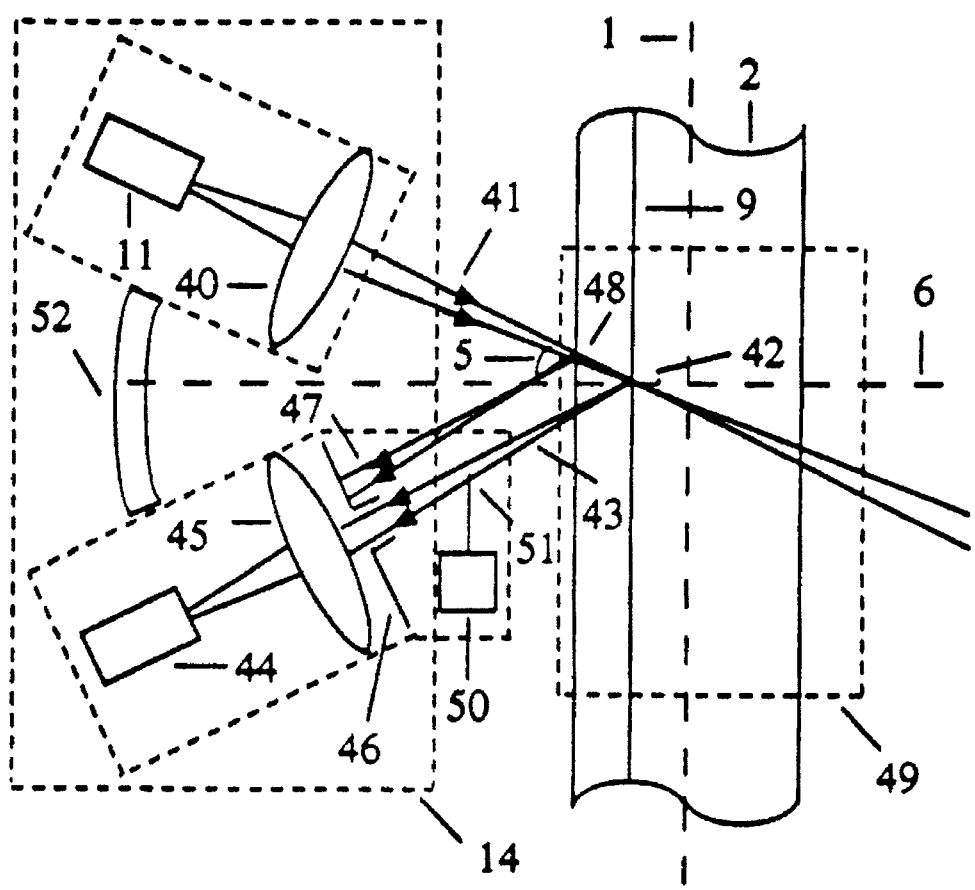
FIGS. 4 is a diagram of the projection of an alternative embodiment of the present invention in the measurement plane, in which the region selecting means includes reflection focusing means, the region scanning means includes object moving means, and the beam measuring means includes interrupting means.
Figure 5:
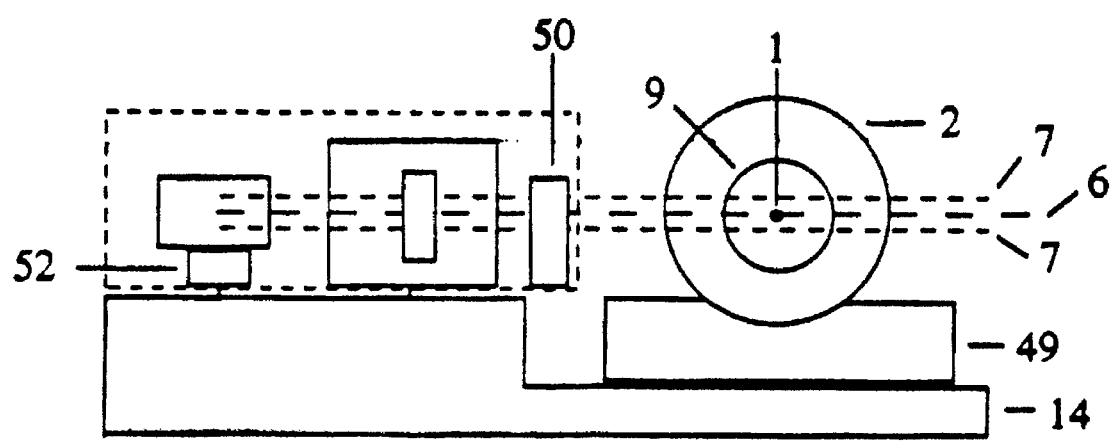
FIGS. 5 is a diagram of the projection of the same embodiment as that of FIG. 4 in the plane orthogonal to an axis of rotational symmetry of the transparent object.

In an alternative embodiment of the present invention, and with reference to FIGS. 4 and 5, a source means, in the form of the laser 11, and an illumination focussing means, in the form of a lens 40, provide an illuminating beam 41, which illuminates a localised radial region 42 at the change of refractive index 9 in the transparent object 2, at the incident angle 5 to the axis 6. A reflected beam 43, reflected from the illuminating beam 41 by the localised radial region 42, falls on a photodetector means 44 via a reflection focussing means, in the form of a lens 45. A beam blocking means 46 prevents a reflected beam 47 from reaching the photodetector means 44, where the reflected beam 47 has been reflected from the illuminating beam 41 by a change in refractive index 48 separate from that at the localised radial region 42. The position of the localised radial region 42 is varied by using an object moving means 49 which positions the transparent object 2 at different positions along the axis 6. An interrupting means is provided in the form of an interruption moving means 50 for moving an opaque screen 51, along a direction parallel to the axis of rotational symmetry 1 of the transparent object 2, so that the reflected beam 43 may either reach the photodetector means 44 or be wholly or partially prevented from doing so by the opaque screen, 51. During use of the apparatus, an aspect of a variation in intensity of the electromagnetic radiation detected by the photodetector means 44 as a function of position of the opaque screen 51 is chosen to represent the position of the reflected beam 43 by the computing means (not shown); for example, the position of the opaque screen 51 at which the intensity falls to half its uninterrupted value. A measurement is then effected by finding the position of this aspect as a function of the incident angle 5 and the localised radial region 42 within the transparent object 2, using the angle altering means 52 and the object moving means 49 under control of the controlling means (not shown). The thicknesses and refractive indices of the layers of the transparent object 2 are then computed as previously described with reference to the apparatus shown in FIG. 1.

Figure 6:
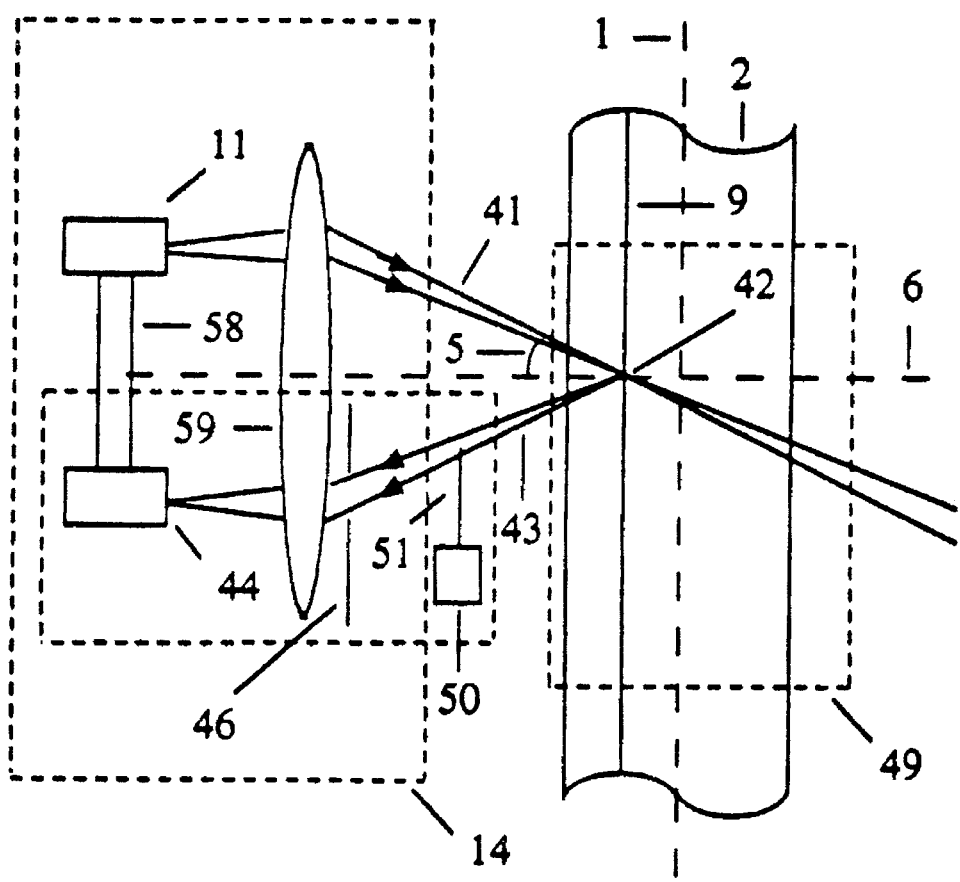
FIGS. 6 is a diagram of the projection of an alternative embodiment of the present invention in the measurement plane, in which the illumination focusing means and the reflection focusing means share a lens.
Figure 7:
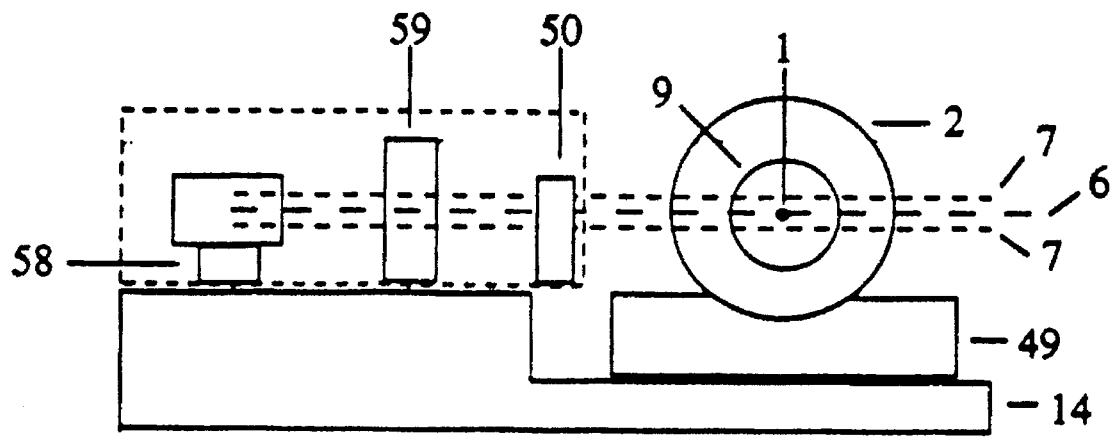
FIGS. 7 is a diagram of the projection of the same embodiment as that of FIG. 6 in the plane orthogonal to an axis of rotational symmetry of the transparent object.

FIG. 6 and FIG. 7 show an alternative embodiment of the present invention, in which the two lenses 40,45 shown in FIG. 4, are combined as a single lens 59, and in which an angle altering means 58 moves both the laser 11 and the photodetector means 44 in a direction parallel to the axis of rotational symmetry 1 to alter the incident angle 5.

Figure 8:
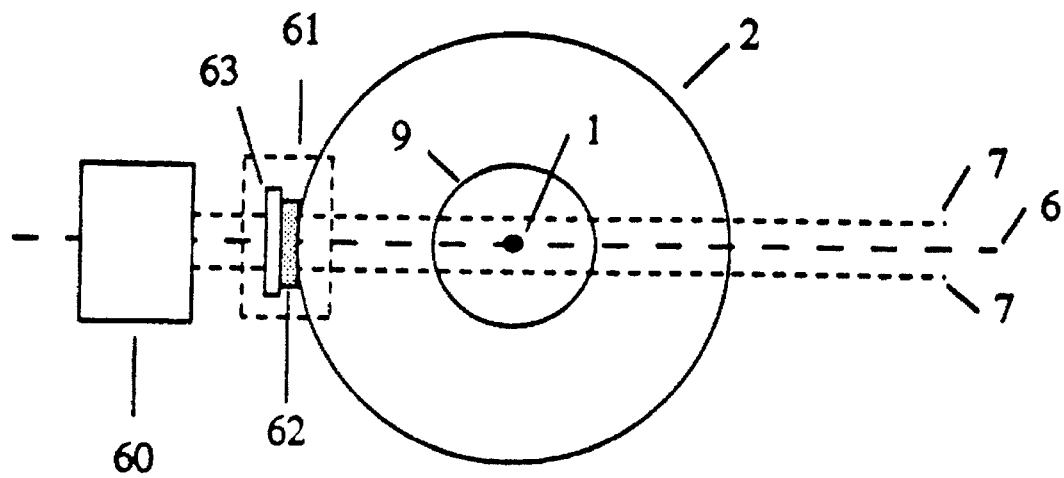
FIG. 8 is a diagram of an embodiment of the optical interface means.
Figure 9:
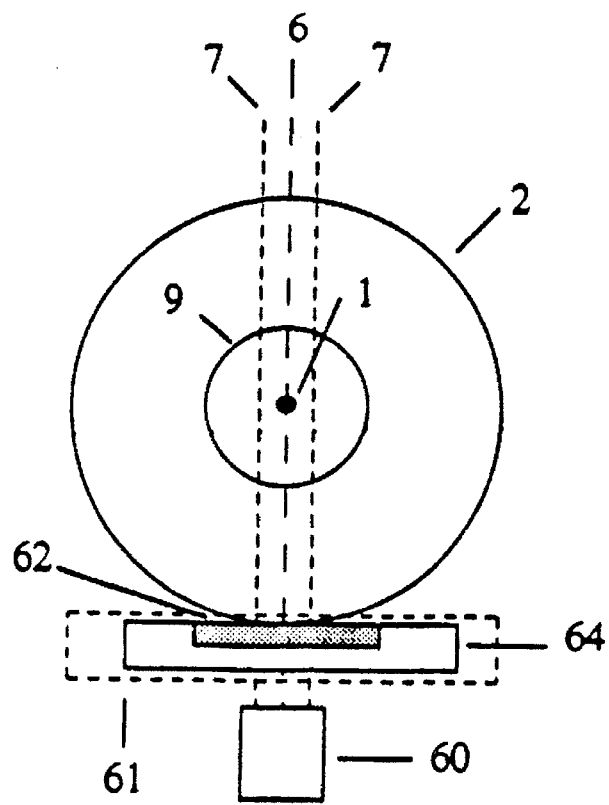
FIG. 9 is a diagram of a further embodiment, of the optical interface means in which refractive index material may be retained by gravity.

FIGS. 8 and 9 show embodiments of the optical interface means suitable for enhancing the performance of the current invention, and these diagrams should be considered in conjunction with FIGS. 1, 2, 4, 5, 6 and 7. With reference to FIG. 8, the optical interface means 61 comprises a solid interface means 63 and a volume of refractive index material 62. The solid interface means 63 is a thin plane of glass, such as a microscope cover slip, with high quality optical surfaces, and is positioned close to transparent object 2 with its orthogonal axis to its surfaces coincident with the axis 6 of the transparent object 2. The solid interface means 63 is also such that the illuminating beam and reflected beam always pass through it during measurement. The volume of refractive index material 62 joins the solid interface means 63 to the transparent object 2, preferably such that no additional support is required for the solid interface means 63, and may be any optical material with a suitable refractive index. With reference to FIG. 9, the optical interface means 61 comprises a solid interface means 64 and a volume of refractive index material 62. The solid interface means 63 is a thin plane of glass, such as a microscope cover slip, with high quality optical surfaces, and is positioned close to transparent object 2 with its orthogonal axis to its surfaces coincident with the axis 6. In addition, the part of the solid interface means 64 which is not in the measurement plane 7 is shaped so that the volume of refractive index material 62 may be retained by gravity when the axis 6 is vertical, or close to vertical.

It is to be appreciated that the embodiments of the invention described above with reference to the accompanying drawings have been given by way of example only and that modifications and additional components may be provided to enhance the performance of the apparatus. Thus, for example, the apparatus may include means for improving the signal to noise ratio of the measurement. Such means may comprise opaque screens positioned to exclude stray electromagnetic radiation, and/or may include modulation means, such as a mechanical chopper or electro-optic modulator or acousto-optic modulator, together with coherent detection apparatus, such as a lock-in amplifier.

I claim:

1. Apparatus for the measurement of optical properties of a quasi cylindrically symmetric transparent object, which apparatus comprises source means for providing a source of electromagnetic radiation, illumination forming means for forming an illuminating beam of electromagnetic radiation for illuminating the transparent object, region selecting means for selecting a localised radial region within the transparent object illuminated by the illuminating beam, region scanning means for scanning the localised radial region through a range of radial positions within the transparent object, reflection detecting means for detecting a reflected beam of electromagnetic radiation reflected out of the illuminating beam at the localised radial region, beam measuring means for measuring the component of the position of the point where the reflected beam leaves the transparent object along a direction parallel to an axis of rotational symmetry of the transparent object, supporting means which causes the illuminating beam, the reflected beam and an axis of rotational symmetry of the transparent object to lie in a measurement plane whose thickness is generally small compared with the radius of the transparent object, angle altering means for altering the angle of incidence of the illuminating beam on the transparent object within the measurement plane, control means for controlling the components of the apparatus such that the measurements are made at the required time and in the required sequence, and computing means for computing optical properties of the transparent object.

2. Apparatus according to claim 1 in which the source means is such that the wavelength of the electromagnetic radiation is variable.

3. Apparatus according to claim 1 in which the supporting means includes adjusting means for adjusting the thickness of the measurement plane to be of the least thickness that is permitted by the dimensions of the illuminating beam, the reflected beam, and the transparent object, and by the degree of cylindrical symmetry of the transparent object.

4. Apparatus according to claim 1 in which the supporting means includes object translating means for translating the transparent object in the measurement plane relative to the apparatus along an axis of rotational symmetry of the transparent object.

5. Apparatus according to claim 1 in which the supporting means includes object rotating means for rotating the transparent object in the measurement plane relative to the apparatus around an axis of rotational symmetry of the transparent object.

6. Apparatus according to claim 1 in which the region scanning means includes object moving means for moving the transparent object relative to other components of the apparatus along a direction orthogonal to an axis of rotational symmetry of the transparent object and within the measurement plane such that the localised radial region in the transparent object may be located over a range of radial positions.

7. Apparatus according to claim 1 in which the illumination forming means includes illumination collimating means for collimating the illuminating beam for illumination of the transparent object, and in which the region selecting means, region scanning means, reflection detecting means and the beam measuring means form detector array means for measuring the component of the position of the point at which the reflected beam falls on the detector array means along a direction parallel to an axis of rotational symmetry of the transparent object, and the apparatus being such that the detector array means converts the spatial distribution of electromagnetic radiation incident upon it into an electrical signal.

8. Apparatus according to claim 6 in which the illumination forming means includes illumination focusing means for focusing the illuminating beam to form the localised radial region within the transparent object, in which the reflection detecting means includes photodetector means for converting electromagnetic radiation into an electrical signal, in which the region selecting means includes reflection focusing means for focusing the reflected beam on to a sensitive surface of the photodetector means, and in which the beam measuring means includes interrupting means for interrupting the reflected beam such that different parts of the reflected beam, with respect to a direction parallel to an axis of rotational symmetry of the transparent object, are prevented from reaching the photodetector means.

9. Apparatus according to claim 8 in which the interrupting means is a chopper wheel.

10. Apparatus according to claim 8 in which the region selecting means includes beam blocking means for preventing reflected beams reaching the photodector means without affecting the reflected beam from the localised radial region being measured.

11. Apparatus according to claim 1 and including optical interface means for producing a well-defined optical interface between the illuminating and reflected beams and the surface of the transparent object such that the optical effects of imperfections at the surface of the transparent object are reduced.

12. Apparatus according to claim 11 in which the optical interface means comprises a solid interface means and a volume of refractive index material so as to form an optical interface to only that small portion of the circumference of the transparent object that is passed through by the illuminating and reflected beams.

* * * * *